United States Patent [19]

Trombley

[11] 3,964,470

[45] June 22, 1976

[54] PERCUTANEOUS INTRADERMAL ELECTRICAL CONNECTION SYSTEM AND IMPLANT DEVICE

[75] Inventor: Michael A. Trombley, Minneapolis, Minn.

[73] Assignee: Medtronic, Inc., Minneapolis, Minn.

[22] Filed: July 25, 1974

[21] Appl. No.: 491,785

[52] U.S. Cl. ............................ 128/2.1 E; 128/418; 128/DIG. 4; 3/1.1
[51] Int. Cl.² ...................... A61B 5/04; A61N 1/36
[58] Field of Search .......... 128/418, 419 P, 419 PS, 128/419 C, 419 E, 2.1 E, 2.06 E, 1 R, DIG. 4, 404; 339/12 R; 3/1, 1.1

[56] References Cited
UNITED STATES PATENTS

| | | | |
|---|---|---|---|
| 3,085,577 | 4/1963 | Berman et al. | 128/418 |
| 3,336,919 | 8/1967 | Russ | 128/418 |
| 3,500,823 | 3/1970 | Richardson et al. | 128/2.06 E |
| 3,663,965 | 5/1972 | Lee et al. | 128/1 R |
| 3,722,005 | 3/1973 | Cowland | 128/418 |
| 3,749,101 | 7/1973 | Williamson | 128/418 |
| 3,760,332 | 9/1973 | Berkovits | 128/418 |
| 3,783,868 | 1/1974 | Bokros | 128/2 R |
| 3,810,258 | 5/1974 | Mathauser | 339/12 R |

FOREIGN PATENTS OR APPLICATIONS

| 1,219,017 | 1/1971 | United Kingdom | 128/419 P |
|---|---|---|---|

OTHER PUBLICATIONS

Kadefors et al., "Percutaneous Electrode...Humans", Med. & Bio. Eng., vol. 8, No. 2, pp. 129–135, 1935.

*Primary Examiner*—Robert W. Michell
*Assistant Examiner*—Lee S. Cohen
*Attorney, Agent, or Firm*—Wayne A. Sivertson; Lew Schwartz

[57] ABSTRACT

A percutaneous intradermal electrical connection system and implant device, the implant device including a flange and a neck extending from the flange. The neck has a cavity in its end and is provided with a lip for inhibiting the growth of epithelial or connective tissue over the neck cavity. A connecting device is partially housed within the neck cavity and allows a lead connected to the implant device to rotate through 360°. The entire surface of the implant device may be electrically conductive and connected to the lead or, alternatively, the implant device may be provided with a separate electrode portion with the remainder of its surface being electrically insulated from the lead. In a preferred embodiment, the implant device is a unitary titanium member whose surface may be partially anodized to provide an insulated surface and establish the separate electrode portion. A preferred connecting device embodiment is magnetic.

24 Claims, 6 Drawing Figures

PERCUTANEOUS INTRADERMAL ELECTRICAL CONNECTION SYSTEM AND IMPLANT DEVICE

BACKGROUND OF THE INVENTION

The infection-free passage of a device through the skin as an electrode or interface offers tremendous advantages in the context of modern medical engineering assist devices. For example, such a device offers the possibility of a connect-disconnect system in conjunction with an implanted electrical device or electrode. Such a system may be employed with an implanted electrical device to recharge an implanted rechargeable power source or, alternatively, may be used with an external power source to allow a power source change without disturbing the implant. As a monitoring electrode, such a device will provide purer bioelectric signals than is obtainable by way of surface electrodes. Additionally, such devices may be employed to electrically activate nerves and muscles for such purposes as pain suppression and motor control.

Percutaneous intradermal implant devices for electrical stimulation are known to the prior art. Such devices take the basic form of a flange having an extending neck. The neck is provided with a cavity through which an electrical connection to the implant device is made. Typically, such prior art devices are made of vitreous carbon which requires extensive processing under rigidly controlled conditions. The final product is not machinable and is dimensionally imprecise. For these reasons, the prior art vitreous carbon implant devices have had a fixed electrical connection to an external lead which is typically accomplished with a conductive epoxy. Other connection systems are under investigation which will provide a non-permanent connection between the lead and the implant device and allow a rotation, through 360°, of the lead relative to the implant device.

SUMMARY OF THE PRESENT INVENTION

The present invention provides an implant device including a flange and a neck extending from the flange a sufficient distance to pass through the skin. The neck has a cavity in its end and is provided with a lip for inhibiting the growth of epithilial or connective tissue over the neck end. The neck cavity houses at least a portion of a connection system for mechanically and electrically connecting a lead to the implant device while allowing the lead to rotate through 360°. In a preferred embodiment, the connection system is magnetic with a magnetic material being housed within the neck cavity. A preferred form of the implant device of the present invention is a unitary titanium member. A portion of the surface of the titanium implant device may be anodized to provide its surface with an electrically insulating coating with the unanodized portion operating as an electrode.

The many objects, advantages and novel features of the present invention will become apparent from the following description when considered in conjunction with the accompanying drawings.

DETAILED DESCRIPTION OF THE DRAWINGS

It is to be understood that the term magnet, as used herein, is intended to include those materials which produce a magnetic field external to themselves while the term magnetic is intended to include magnets and those materials which are attracted by a magnetic field.

Figure 1:
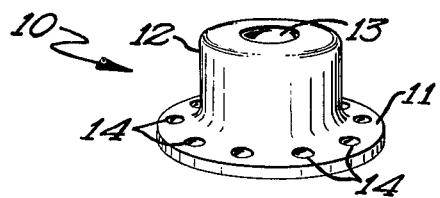
FIG. 1 illustrates in perspective a prior art implant device.

FIG. 1 illustrates a prior art percutaneous implant device 10. The device includes a flange 11 having a neck 12 extending from its center. The neck is provided with a cavity 13 in its end and the flange has a series of apertures 14. The height of the neck 12 is sufficient to pass through the skin at the desired placement location, the height being variable dependent on skin thickness. Also, the device may be used without the apertures 14, although it has been found that the apertures provide a resistance to torque forces thereby reducing the possibility of extrusion of the device.

Typical prior art devices conforming to the configuration of FIG. 1 are made of vitreous carbon. This material is produced after extensive processing under conditions which must be rigidly controlled. The final material is not machinable and the final product has a very poor dimensional consistency from one device to the next. For these reasons, the connection to an external lead is typically made by a permanent connection to the neck, most often through the use of a conductive epoxy filling the cavity 13 and connecting the implant device to the external lead.

Figure 2:
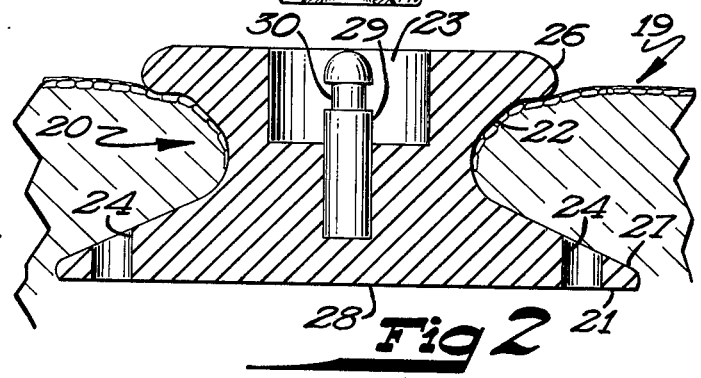
FIG. 2 illustrates in partial corss section elevation a preferred embodiment of an implant device in intradermal position after surgical implantation and its external connection system in accordance with the present invention.

FIG. 2 illustrates a preferred embodiment of a percutaneous intradermal device 20 and a connector 25 implanted in the skin 19 of a human in a manner well known in the art. The implant device has a subcutaneous flange 21 from which a neck 22 extends. The neck has a cavity 23 in its end and a series of apertures 24 pass through the flange 21 in a manner similar to the apertures 14 illustrated in FIG. 1. The neck 22 is provided with a lip 26 which extends outwardly from the neck approximately 40 thousandths of an inch. This lip 26 acts to inhibit the growth of epithilial tissue over the end of the neck to prevent its interference with the connection system. Of course, lips extending a great distance from the narrowest portion of the neck would have a greater inhibiting effect. It has been found, however, that a 40 thousandths lip extension sufficiently inhibits the epithilial overgrowth without making the upper portion of the neck unduly large. Also, the height of the neck may be variable to accommodate different skin thicknesses. It is contemplated that a neck height of 250 thousandths of an inch will pass through the skin at all body locations while a 200 thousandths neck extension may be all that is required in some applications.

As discussed above, the apertures 24 operate to reduce the likelihood of an extrusion of an implant device after placement. It has also been found that the angle of the upper surface 27 of the flange 21 relative to the bottom surface 28 of the flange 21 can affect the permanency of the device. That is, devices with an angle of approximately 10°±2° between the surfaces 27 and 28 have a lower occurrence of extrusion than is the case when that angle exceeds approximately 10°±2°.

The connector 25 is aperture to cooperate with a pin 29 which is press fit in the bottom of the cavity 23. The pin 29 is provided with a detent 30 and the connector 25 is provided with spring-like members which engage the detent 30 to releasably secure the connector 25 in position while maintaining an electrical contact with the pin 29. The cap portion 31 of the connector 25 is provided with an aperature which slips over the pin 29 with its internal spring members engaging the detent 30 to secure the connector 25 in position. The connector 25 also establishes an electrical connection between the pin 29 and an external lead 32, the lead being adapted for connection to an external electrical device in known manner. For convenience, the lead 32 may have a length of 2-3 inches and be provided with another suitable connector for connection to a lead from the electrical device itself. The connector may be provided with a Teflon ring 33 at its face which engages the upper portion of the neck 22 for reasons to be discussed more fully below.

The implant device embodiment illustrated in FIG. 2 is illustrated as a metallic member. For the application contemplated for the present invention, the material chosen for the implant device must be a body-compatible; namely, substantially inert to living body tissue and fluids. A material meeting these constraints is titanium which has been found suitable for use in the implant device illustrated in FIG. 2.

Figure 3:
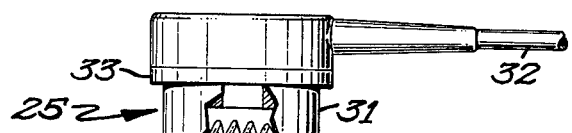
FIG. 3 illustrates another preferred embodiment of the present invention.
Figure 3:
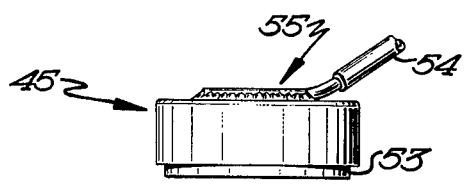
Figure 3:
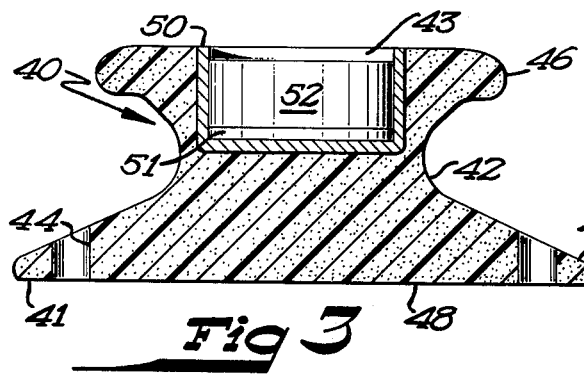

Referring now to FIG. 3, there is shown another preferred embodiment of the present invention. Specifically, FIG. 3 illustrates an implant device 40 and connector 45. The implant device 40 has a flange 41 and an extending neck 42. The upper and lower surfaces of the flange 41, 47 and 48, respectively, form an angle of approximately 10°±2°, as described with reference to FIG. 2. The neck 42 is provided with a lip 46 of approximately 40 thousandths of an inch and has a cavity 43 in its end. A series of apertures 44 extend around the circumference of the flange 41.

For reasons to be explained more fully, below, the cavity 43 of neck 42 is lined with a non-magnetic body-compatible material 50. Examples of such materials are those stainless steels whose reference numbers are below 400. Positioned at the bottom of the cavity and over the liner 50 is a magnetic body-compatible plate 51. The plate 51 may be a 400 series stainless steel and is permanently secured within the cavity 43 as by press fitting, for example. A magnetic material 52 bills the bulk of the remainder of the cavity 43.

The connector 45 is a magnetic material having a portion 53 configured to fit within the unfilled portion of the recess 43. Of course, one or both of the magnetic material 52 and connector 45 must be a magnet in order that a mechanical connection is made between them when the extending portion 53 is placed within the cavity 43 and into contact with the magnetic material 52. If the connector 45 is a magnet, its connection to the wire 54 from an external electrical device can be facilitated by plating it with gold to allow a soldered connection such as that illustrated at 55. Of course, any other suitable type of connection between the conductor 54 and the connector 45 may be employed.

As illustrated, the extending portion 53 will fit within the cavity 43 and into physical contact with the magnetic material 52 to establish a mechanical and electrical connection between the implant device 40 and the lead 54. The extending portion 53 will provide security against a lateral force separating the connector 45 and the magnetic material 52. Alternatively, the magnetic material 52 may extend out of the cavity 43 above the height of the neck 42 while the connector 45 is provided with a recess configured to accept the extending portion of the magnetic material 52. In this manner, the same security against a separation of the magnetic material 52 and the connector 45 is obtained while the cavity 43 is eliminated as a collector of debris.

The non-magnetic cavity liner 50 operates as a "keeper" in a manner known to the prior art. Where such a keeper is deemed unnecessary, it may be eliminated without departing from the scope of the present invention. Also, the magnetic material 52 may be secured within the cavity 43 without the use of the plate 51 in any convenient manner, the plate 51 being employed principally when the member 52 is a magnet, the magnetic attraction between the plate 51 and the magnet tending to hold the member 52 in place.

The material contemplated for use in the embodiment of FIG. 3 is a low temperature isotopic (LTI) carbon deposited on a graphite core. Such materials are known to the prior art and have the advantage over vitreous carbon of being machinable at least to the extent of the amount of carbon deposited on the graphite core. Of course, the LTI carbon implant device illustrated in FIG. 3 may be employed with the pin connector 29 illustrated in FIG. 2 while the magnet connection of FIG. 3 may be employed with the titanium implant device embodiment illustrated in FIG. 2 without departing from the scope of the present invention.

The implant device configurations illustrated in FIGS. 2 and 3 are, together with the prior art device illustrated in FIG. 1, intended to provide an electrical stimulation to the general area surrounding the location of their placement. Percutaneous stimulation for pain suppression is an example of a use for such an implant device. On occasion, it may be necessary to provide a more localized stimulation as for nerve or muscle stimulation for motor control. Examples of devices for such use are illustrated in FIGS. 4 and 5.

Figure 4:
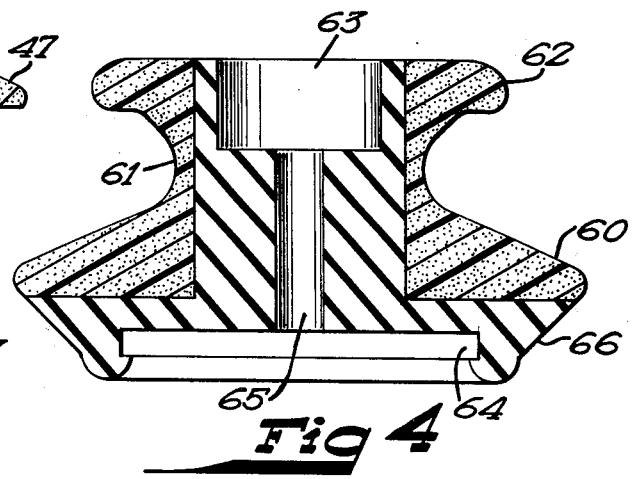
FIG. 4 illustrates still another preferred embodiment of the present invention.

FIG. 4 illustrates an implant device intended for localized stimulation employing an LTI carbon and includes a flange 60 and an extending neck 61 having a lip 62 and cavity 63. Either of the electrical connection systems of FIGS. 2 and 3 may be employed within the cavity 63 to provide an electrical and mechanical connection to an external electrical device. Similarly, the lip 64 is as illustrated in FIGS. 2 and 3. In the embodiment of FIG. 4, an electrode plate 64 is provided on the bottom surface of the implant device and has a connecting post 65 passing through the implant device body to the cavity 63 for connection to the connector system. If the connector system is to be the pin type illustrated in FIG. 2, the member 65 may extend into the cavity 63 and itself form the pin. Alternatively, if the magnet connector system of FIG. 3 is employed the member 65 will make an electrical contact with the lowermost member of the connection system thereby connecting the plate 64 to the lead from the external electrical device. The LTI carbon flange 60 and neck 61 are insulated from the plate 64 and member 65 by an insulating material 66. Along with being electrically insulating, the material 66 should be body-compatible and, if the member 66 is to be molded, the material should be sufficiently viscous such that it can be evacuated. Within these constraints, any material known to the prior art may be employed.

Within the embodiment of FIG. 4, by making electrical contact with the member 65 only the plate 64 will be electrically connected to the external electrical device. Thus, the electrical stimulation will be more directional and thus more localized as may be required for motor control, for example. To assure that electrical contact is not made between either the connector 25 (see FIG. 2) or 45 (see FIG. 3) the connector should be insulated at the point where it engages the upper portion of the neck 61. This may be accomplished with either the connector 25 or the connector 45 by means of an insulating member such as that illustrated at 33 in FIG. 2. A similar member may be applied to the connector 45 of FIG. 3 when that connector is used in conjunction with the embodiment of FIG. 4 and, with each connector, will assure an electrical contact only with the member 65.

Figure 5:
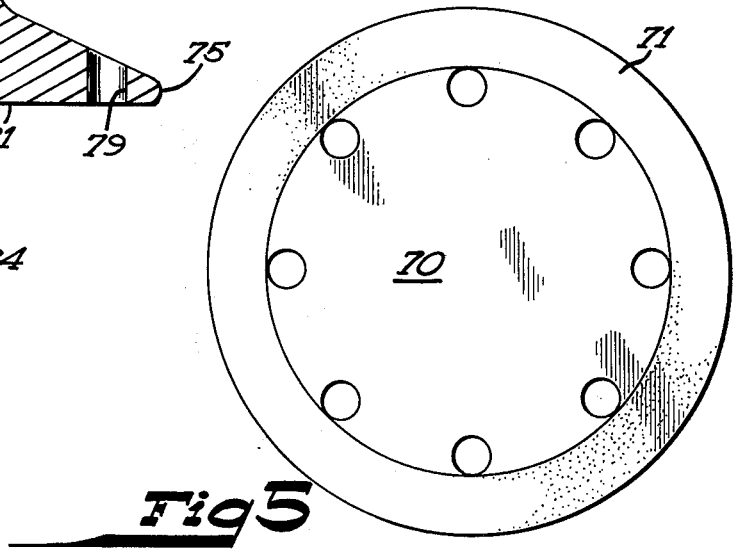
FIG. 5 illustrates a bottom view of a modification of the embodiment of FIG. 2.

FIG. 5 illustrates a modification of the embodiment of FIG. 2 which will accomplish the localized stimulation obtained with the embodiment of FIG. 4. The titanium implant device 20 of FIG. 2, with either connection system as illustrated in FIGS. 2 and 3, is anodized to provide an insulating coating over a large portion of the implant device surface. As illustrated in FIG. 5, a portion of the underside of the flange 21 is masked leaving that portion 70 unanodized while the remainder 71, including the upper surface 27 of the flange 21 and the neck 22 (see FIG. 2) is anodized to provide an electrically insulating coating thereon. Thus, the unanodized portion 70 operates in a manner similar to the plate 64 of the embodiment of 64 to provide a localized stimulation. It has been found that an anodizing solution of concentrated sodium ammonium phosphate in distilled water will produce an insulating surface coating of titanium oxide which is substantially inert to living body tissues and fluids. An anodizing operation employing titanium positive and indifferent electrodes with the positive electrode attached to the part to be anodized and a voltage of 35 volts with the current set to full scale will produce a coating of titanium oxide which functions as a suitable electrical insulation at the tissue interface. It may also be desirable to chemically polish the anodized surface inasmuch as the smoother surface produced by the polishing process results in a smaller tissue build up after implant. It has been found that a polishing solution of seven parts of 52% nitric acid and one part of concentrated hydroflouric acid produces the desired surface conditions. The nitric acid is preheated to 140°F in a glass beaker and then is poured into a plastic beaker into which the hydroflouric acid is added. The polishing operation is completed in this solution after 15 seconds.

Figure 6:
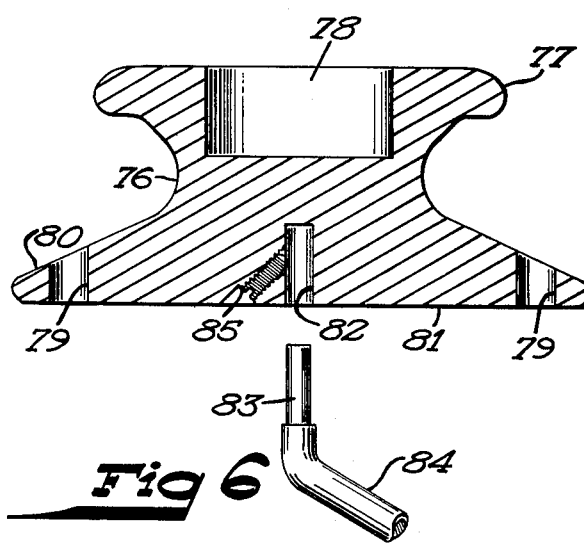
FIG. 6 illustrates a modification of the preferred embodiment of FIGS. 2 or 3.

Referring now to FIG. 6 there is shown an implant device capable of functioning as a percutaneous interface between an implanted device such as an electrode or implanted electronic circuitry. The device has a flange 75, neck 76, lip 77 and cavity 78 as discussed above with reference to FIGS. 2–4. The cavity 78 may contain the pin or magnetic connection system components discussed above and the flange 75 may be provided with the apertures 79 while its upper and lower surfaces 80 and 81, respectively, should have the angular relationship discussed above. The percutaneous interface implant device illustrated in FIG. 6 may be constructed of titanium with its entire surface anodized and chemically polished as discussed with reference to FIG. 5. In this manner, the implant device is provided with an insulating layer of titanium oxide over its entire surface. The bottom surface of the implant device is provided with a bore 82 of a size which will accept the exposed end 83 of a lead 84. A set screw 85 is provided for securing the exposed end 83 within the bore 82 in known manner. Of course, the surface of the bore 82 should be bare so as to make an electical contact with the exposed end 83 of the lead 84.

With the exposed end 83 of lead 84 secured within the bore 82 via the set screw 85, and with one of the connection systems of FIG. 2 or FIG. 3 establishing a mechanical and electrical contact with the lead from an external electrical device, that device is electrically connected to the lead 84. The lead 84 may terminate at electrodes adapted to stimulate a particular muscle or nerve. For example, through the use of an interface such as that illustrated in FIG. 6 the lead 84 may terminate at an electrode secured to the heart and the heart may be paced via an external pacemaker through the interface. Alternatively, other muscles or nerves may be stimulated with electrodes of the type presently employed for specific applications which hertofore having required an implantation of the stimulation generating devices as well. Additionally, the lead 84 may be connected to a rechargeable power source within an implanted device and used periodically to recharge that power source while eliminating the necessity to surgically expose the implant or it may be used to connect an external power source to an implanted electrical device.

Many modifications and variations of the present invention are possible in light of the above teachings. For example, the interchangeability of the illustrated connection systems and their use with the various implant device embodiments is within the scope of the present invention. It is therefore to be understood that, within the scope of the appended claims, the invention may be practiced otherwise than as specifically described.

What is claimed is:

1. In a percutaneous electrical connection system of the type having a conductive lead, having an implant device including a flange and a neck extending from the flange a sufficient distance to pass an end thereof through the skin, the neck being provided with a cavity in said end and said implant device including an electrical conduction path from its neck cavity to at least one location at the surface of its flange, and having means for operatively connecting said lead to said implant device, the improvement wherein said connecting means includes first and second means for releasably establishing a mechanical and electrical connection between said lead and said implant device conduction path while allowing said lead to rotate through 360° relative to said implant device, said first means being secured within said cavity in electrical communication with said implant device conduction path and said second means being secured to said lead in electrical communication therewith.

2. The system of claim 1 wherein said flange is formed of upper and lower surfaces, said flange surfaces forming an angle of approximately 10°.

3. The system of claim 1 wherein said flange is formed of upper and lower surfaces, said flange surfaces forming an angle no greater than about 10°.

4. The system of claim further comprising localized stimulation electrode means in electrical communication with said implant device conduction path at the flange surface.

5. The system of claim 4 wherein said flange is formed of upper and lower surfaces, said electrode means comprising electrode plate means on the lower surface of said flange.

6. The system of claim 4 wherein said implant device is a unitary structure of a conductive material, said flange being formed of upper and lower surfaces with said neck and flange upper surface being provided with an insulating coating and at least a portion of said flange lower surface forming said electrode means.

7. The system of claim 1 wherein said first and second means comprise magnetic means.

8. The system of claim 1 wherein said first means comprises a magnetic material and said second means comprises magnetic means secured to said lead, at least one of said magnetic material and said magnetic means being a magnet.

9. The system of claim 8 wherein said neck cavity is lined with a keeper.

10. The system of claim 9 wherein said magnetic material fills only a portion of said neck cavity, said magnetic means having a portion configured to fit into said neck cavity and into physical contact with said magnetic material.

11. The system of claim 8 wherein said neck cavity is lined with non-magnetic stainless steel.

12. The system of claim 8 wherein said magnetic material fills only a portion of said neck cavity, said magnetic means having a portion configured to fit into said neck cavity and into physical contact with said magnetic material.

13. The system of claim 8 wherein said magnetic means comprises a gold plated magnet.

14. The system of claim 1 wherein said first means comprises pin means and said second means comprises means for releasably engaging said pin means.

15. The system of claim 14 wherein said pin means is provided with detent means and said engaging means comprises means for releasably engaging said detent means.

16. The system of claim 1 wherein said implant device flange and neck are unitary and are formed of a conductive material.

17. The system of claim 16 wherein said conductive material is low temperature isotopic carbon.

18. The system of claim 16 wherein said conductive material is titanium.

19. The system of claim 7 wherein at least a portion of the titanium surface is anodized.

20. The system of claim 19 wherein the anodized titanium surface is chemically polished.

21. The system of claim 1 wherein said implant device flange is provided with an electrode portion at its surface, said electrode portion being electrically connected to said lead through said connecting means and said implant device conduction path.

22. The system of claim 21 wherein said implant device flange and neck are unitary and are formed of titanium, less than the entire surface of said implant device being anodized with the non-anodized implant device surface forming said electrode portion.

23. The system of claim 22 wherein the anodized implant device surface is chemically polished.

24. The system of claim 1 wherein said implant device flange is provided with means for securing an electrode lead at the flange surface, said implant device conduction path extending between said neck cavity and said electrode lead securing means.

* * * * *

UNITED STATES PATENT AND TRADEMARK OFFICE
CERTIFICATE OF CORRECTION

PATENT NO. : 3,964,470
DATED : June 22, 1976
INVENTOR(S) : Michael A. Trombley, Minneapolis, Minn.

It is certified that error appears in the above—identified patent and that said Letters Patent are hereby corrected as shown below:

Column 3, line 5, "aperture" should be -- adapted --.

Column 3, line 12, "aperature" should be -- aperture --.

Claim 4, line 1, after "claim" insert -- 1 --.

Signed and Sealed this

Twenty-eighth Day of December 1976

[SEAL]

Attest:

RUTH C. MASON
Attesting Officer

C. MARSHALL DANN
Commissioner of Patents and Trademarks